(12) United States Patent
Oommen et al.

(10) Patent No.: US 9,810,631 B2
(45) Date of Patent: *Nov. 7, 2017

(54) WAVELENGTH SCANNING APPARATUS AND METHOD OF USE THEREOF

(71) Applicant: STEM ARTS PROJECTS, LLC, Lincoln, NE (US)

(72) Inventors: Abraham Oommen, Lincoln, NE (US); Matthew Greenleaf, Lincoln, NE (US); Adam Koch, Lincoln, NE (US); Amitabha Sarkar, Lincoln, NE (US)

(73) Assignee: STEM ARTS PROJECTS, LLC, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/340,274

(22) Filed: Nov. 1, 2016

(65) Prior Publication Data

US 2017/0115222 A1 Apr. 27, 2017

Related U.S. Application Data

(63) Continuation-in-part of application No. 14/809,175, filed on Jul. 25, 2015, now Pat. No. 9,568,429.

(51) Int. Cl.
*G01N 21/64* (2006.01)
*C12Q 1/68* (2006.01)

(52) U.S. Cl.
CPC ....... *G01N 21/6428* (2013.01); *C12Q 1/6818* (2013.01); *G01N 21/6452* (2013.01);
(Continued)

(58) Field of Classification Search
CPC ........... G01N 21/6428; G01N 21/6452; G01N 21/6486; G01N 2201/061
See application file for complete search history.

(56) References Cited

U.S. PATENT DOCUMENTS 6,248,988 B1 6/2001 Krantz
8,809,040 B2 * 8/2014 King ................. G01N 21/6428
435/287.1

(Continued)

FOREIGN PATENT DOCUMENTS

WO 2014047737 A1 4/2014
WO 2004048937 A2 6/2014
WO 2014100725 A1 6/2014

OTHER PUBLICATIONS

International Search Report and Written Opinion issued Oct. 26, 2016 for related application PCT/US2016/043052,14 pages.

*Primary Examiner* — Mark R Gaworecki
(74) *Attorney, Agent, or Firm* — Baird Holm, LLP; Arianna Goldstein

(57) ABSTRACT

A wavelength scanning apparatus that detects at least four different fluorescent emission wavelengths simultaneously or nearly simultaneously is described. The wavelength scanning apparatus includes a heating block having at least four sample wells, each sample well configured for receiving a sample, at least four excitation activation apertures, and at least four fluorescence emission discharge apertures. The wavelength scanning apparatus also includes an analysis scanner having at least four light sources, where the at least four light sources excite at least four fluorophores, at least four excitation light filters that filter out light except that of the desired excitation wavelength/s, at least four fluorescence emission light filters that filter out light except that of the desired fluorescent emission wavelengths, and at least four photodetectors to detect light of the desired fluorescent emission wavelengths.

7 Claims, 10 Drawing Sheets

(52) U.S. Cl.
CPC ............... *G01N 2021/6419* (2013.01); *G01N 2021/6421* (2013.01); *G01N 2021/6432* (2013.01); *G01N 2201/10* (2013.01)

(56) References Cited

U.S. PATENT DOCUMENTS

| | | |
|---|---|---|
| 2003/0127609 A1* | 7/2003 | El-Hage ............... G01N 21/253 250/574 |
| 2004/0101851 A1 | 5/2004 | White et al. |
| 2012/0093288 A1 | 4/2012 | Mastronardi et al. |
| 2012/0115214 A1 | 5/2012 | Battrell et al. |

\* cited by examiner

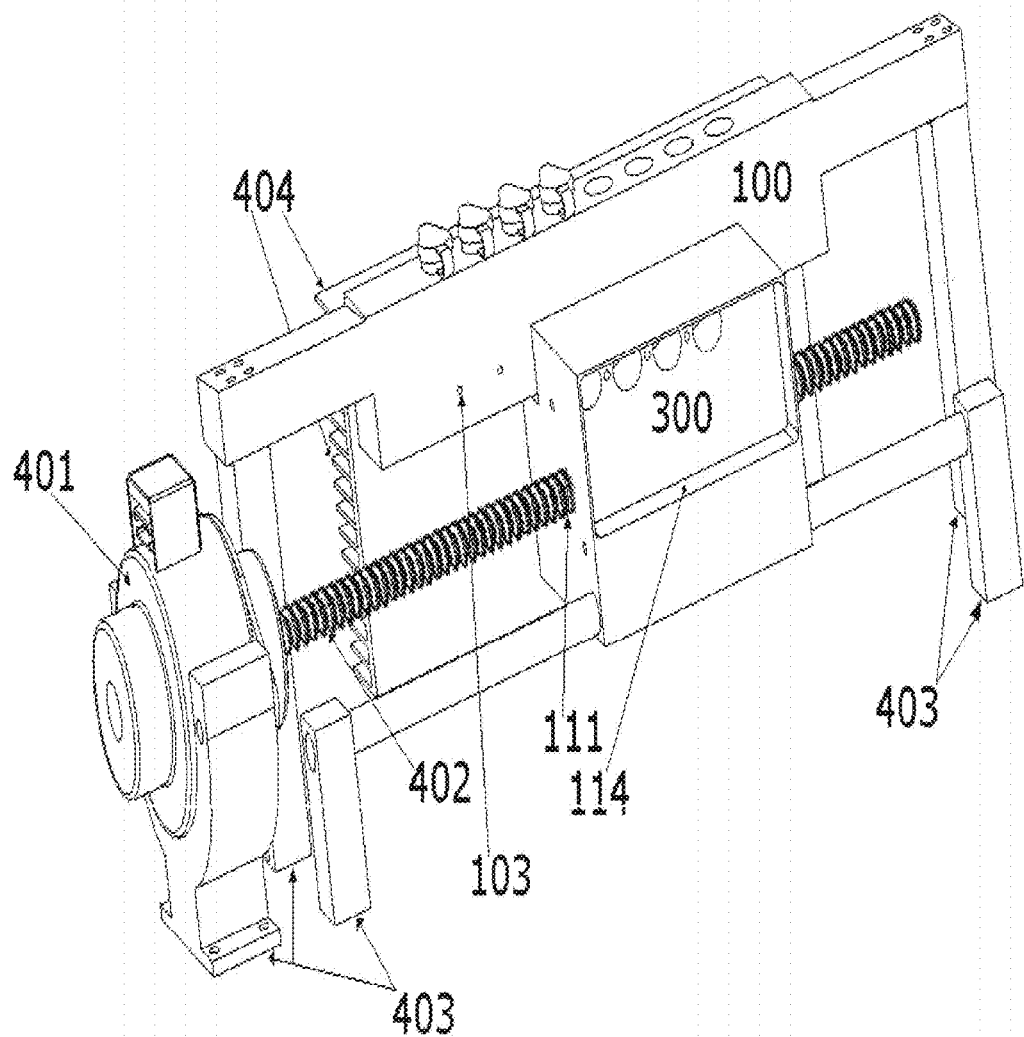

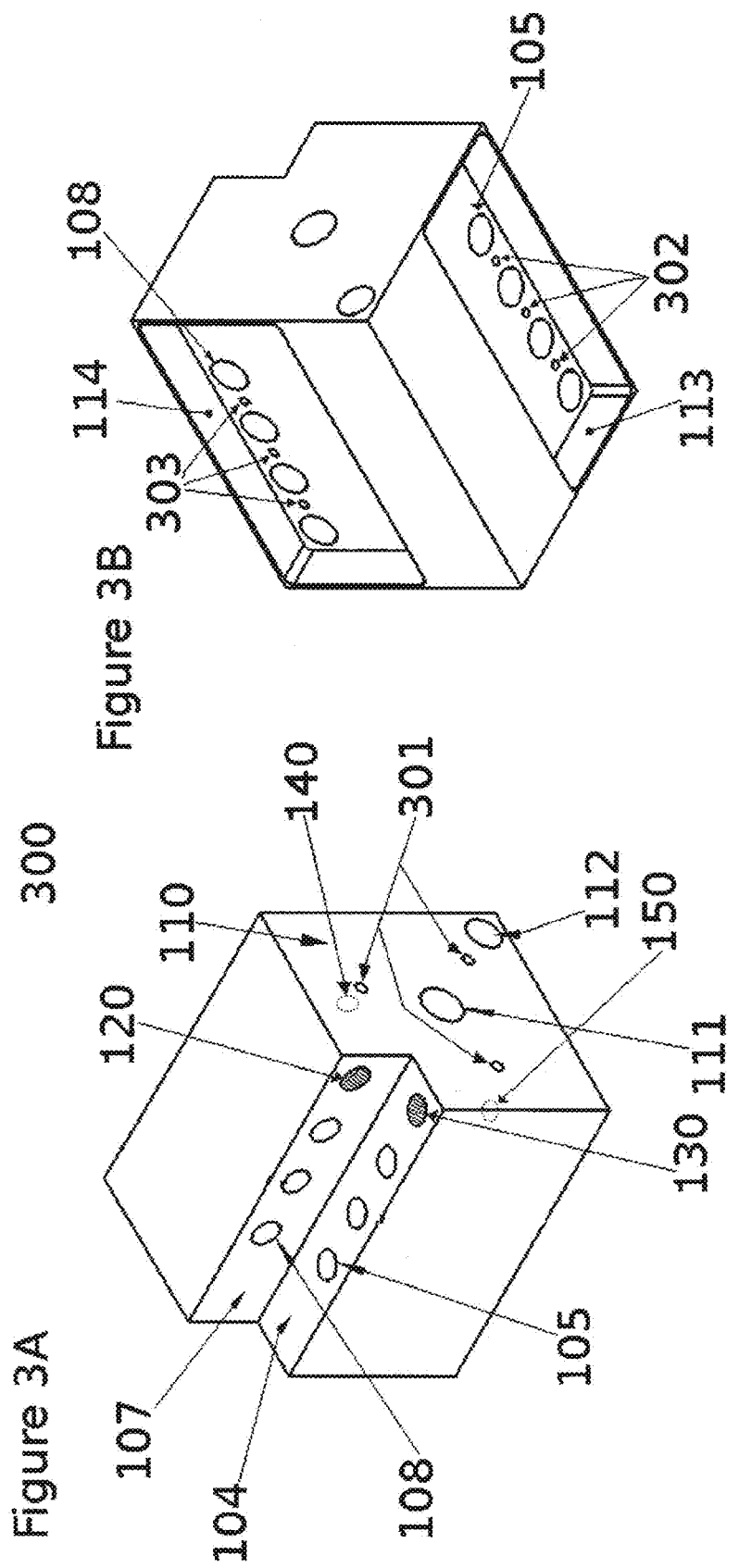

610
First Position

| | | | | | | | |
|---|---|---|---|---|---|---|---|
| Heating Block | | | | 1 | 2 | 3 | 4 |
| Scanner | 1 | 2 | 3 | 4 | | | |

620
Second Position

| | | | | | | | |
|---|---|---|---|---|---|---|---|
| Heating Block | | | | 1 | 2 | 3 | 4 |
| Scanner | | 1 | 2 | 3 | 4 | | |

630
Third Position

| | | | | | | | |
|---|---|---|---|---|---|---|---|
| Heating Block | | | | 1 | 2 | 3 | 4 |
| Scanner | | | 1 | 2 | 3 | 4 | |

640
Fourth Position

| | | | | | | | |
|---|---|---|---|---|---|---|---|
| Heating Block | | | | 1 | 2 | 3 | 4 |
| Scanner | | | | 1 | 2 | 3 | 4 |

650
Fifth Position

| | | | | | | | | |
|---|---|---|---|---|---|---|---|---|
| Heating Block | | | | 1 | 2 | 3 | 4 | |
| Scanner | | | | | 1 | 2 | 3 | 4 |

660
Sixth Position

| | | | | | | | | | |
|---|---|---|---|---|---|---|---|---|---|
| Heating Block | | | | 1 | 2 | 3 | 4 | | |
| Scanner | | | | | | 1 | 2 | 3 | 4 |

670
Seventh Position

| | | | | | | | | | | |
|---|---|---|---|---|---|---|---|---|---|---|
| Heating Block | | | | 1 | 2 | 3 | 4 | | | |
| Scanner | | | | | | | 1 | 2 | 3 | 4 |

1000

WAVELENGTH SCANNING APPARATUS AND METHOD OF USE THEREOF

CROSS-REFERENCE TO RELATED APPLICATIONS

This application claims priority to and is a Continuation-in-Part of U.S. patent application Ser. No. 14/809,175, filed on Jul. 25, 2015, which is expressly incorporated herein by reference in its entirety.

BACKGROUND

Fluorescence detection of nucleic acids and proteins is carried out by a variety of apparatuses and methods, including capillary electrophoresis, deoxyribonucleic acid (DNA) sequencing with fluorescent dyes, and microfluidic fluorescence detection. Methods and apparatus for fluorescence detection of nucleic acids and proteins generally include four common elements: a light source for excitation of fluorophores, a fluorophore capable of excitation and emission, filters to isolate a wavelength emitted from an excited fluorophore, and a detector that detects the emitted wavelength from the excited fluorophore and produces an electrically recordable output.

When methods and apparatus of fluorescence detection are used for nucleic acid detection, such methods may require polymerase chain reaction (PCR) or isothermal amplification to obtain the desired output signal. The fluorescence detection apparatus generally includes a heating block having one or more sample wells configured for receiving vessels where PCR or isothermal amplification may take place. In instances where the heating block has at least two wells, a movable scanning component may be necessary where either the heating block or the detector is moved in order to measure the fluorescence of a sample in each of the different sample wells. Typically, the movable scanning component contains dichroic mirrors, filter wheels, and photomultiplier tubes to direct, isolate, and convert the fluorescence emissions from the samples to an electric output. These components are costly and limit the simultaneous detection of multiple wavelengths. Detection of a single fluorescent emission wavelength increases the time required for measuring fluorescent emission wavelengths from multiple sample wells, thereby decreasing efficiency and increasing the time required to complete the analysis of multiple sample wells.

It is desirable to eliminate expensive parts from the movable scanning component used in fluorescence detection. It is also desirable to provide a fluorescence detection system capable of detecting at least four fluorescent emission wavelength emissions simultaneously or nearly simultaneously.

SUMMARY

An apparatus for fluorescence detection through a wavelength scanning apparatus is described. A wavelength scanning apparatus using fluorescence emissions to test for the presence of at least four nucleic acid sequences or proteins simultaneously or nearly simultaneously also is described.

A nucleic acid analysis method for performing fluorescence detection of multiple fluorescence emission wavelengths simultaneously or nearly simultaneously is also described.

A DNA analysis method for performing fluorescence detection of multiple fluorescence emission wavelengths simultaneously or nearly simultaneously is also described.

The following detailed description is exemplary and explanatory only and is not necessarily restrictive of the invention as claimed. The accompanying drawings, which are incorporated in and constitute a part of the specification, illustrate embodiments of the invention and together with the detailed description, serve to explain the principles of the invention.

BRIEF DESCRIPTION OF THE DRAWINGS

The numerous advantages of the present invention may be better understood by those skilled in the art by reference to the accompanying figures.

FIG. 1 represents a wavelength scanning apparatus.

FIG. 3A is a front angled view of a analysis scanner of the wavelength scanning apparatus.

FIG. 3B is a back angled view of a analysis scanner of the wavelength scanning.

FIG. 6 illustrates alignment of an analysis scanner with a plurality of sample wells.

DETAILED DESCRIPTION

Figure 2A:
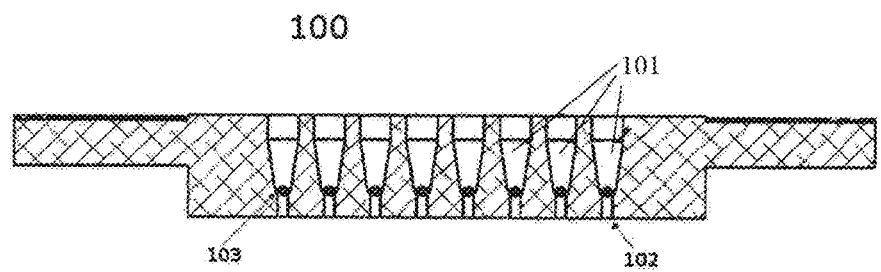
FIG. 2A is a vertical cross sectional view of a heating block of the wavelength scanning apparatus.

A wavelength scanning apparatus that detects at least four fluorescent emission wavelengths simultaneously or nearly simultaneously is described. The wavelength scanning apparatus includes a heating block having at least four sample wells, where each sample well is configured for receiving a sample, at least four excitation activation apertures, and at least four fluorescence emission discharge apertures. The excitation activation apertures and fluorescence emission discharge apertures are arranged in a right angle or nearly a right angle to each other for fluorescence detection. The wavelength scanning apparatus also includes an analysis scanner having at least four light sources, where each of the at least four light sources excites a different fluorophore, at least four excitation light filters that filter out light except that of the desired excitation wavelength/s, at least four fluorescence emission light filters that filter out light except that of the desired fluorescent emission wavelength/s, and at least four photodetectors to detect light of the desired fluorescent emission wavelengths. Each of the at least four light sources may be paired with a different excitation light filter and a different fluorescent emission light filter. The scanner may remain stationary along one face of the heating block for detection of at least four fluorescent emission wavelengths simultaneously or nearly simultaneously. The analysis scanner may move laterally along one face of the heating block to a plurality of predetermined locations for detection of at least four different fluorescent emission wavelengths from each sample. Thus, while the analysis scanner may simultaneously or nearly simultaneously analyze at least four different fluorescent emission wavelengths, the analysis scanner is analyzing one fluorescent emission wavelength from a single sample well at a time. The movement of the analysis scanner laterally along one face of the heating block may be constrained by threaded movement.

FIG. 1 represents a wavelength scanning apparatus 400. The wavelength scanning apparatus 400 comprises a heating block 100, an analysis scanner 300, a stepper motor 401, a stepper screw 402, a stepper screw hole 111, and a structural support 403 having a guide rail 405. The heating block 100 is attached to the structural support 403 via the heating block screw holes 202 such that the heating block 100 is suspended horizontally by the structural support 403. The analysis scanner 300 may be attached to the structural support 403 by insertion of the guide rail 405 through the guide rail hole 112 so that the analysis scanner is suspended horizontally such that the flat surface 104 of the analysis scanner 300 aligns with the bottom of the heating block 100, and the front wall 107 of the analysis scanner 300 aligns with the front of the heating block 100. The bottom of the heating block 100 may nearly contact the flat surface 104 of the analysis scanner 300, and the front of the heating block 100 may nearly contact the front wall 107 of the analysis scanner 300. The bottom of the heating block 100 may contact the flat surface 104 of the analysis scanner 300, and the front of the heating block 100 may contact the front wall 107 of the analysis scanner 300, where such contact by the flat surface 104 and the front wall 107 allows for lateral movement of the analysis scanner 300. The stepper motor 401 may be attached to the structural support 403 such that it is suspended horizontally below the heating block 100. The stepper screw 402 is connected to the stepper motor 401. The structural support 403 may include a rectangular piece of material (e.g. plastic or metal) (not shown) that serves as a base platform and has one or more vertical supports configured for attachment to the heating block 100 via the heating block screw holes, the stepper motor 401, and the guide rail 405. The structural support may include a casing (not shown) configured to enclose the wavelength scanning apparatus 400. In embodiments the casing has a lid or a flap that opens above the heating block 100 configured for introduction of DNA samples into the heating block 100. The casing may be made of any material consistent with the desired operation of the device, such as plastic or aluminum.

The stepper motor 401 is configured for turning the stepper screw 402 a predetermined distance wherein a plurality of excitation apertures 105 of the analysis scanner 300 align with a plurality of excitation activation apertures 102 of the heating block 100, and a plurality of fluorescence emission discharge apertures 103 of the heating block 100 align with a plurality of emission apertures 108 of the analysis scanner 300 (e.g. the geometric centers of these corresponding apertures substantially align, thus sufficiently align for transmission of the desired excitation and emission wavelengths). For example, the excitation aperture 105 substantially aligns with the excitation activation aperture 102 and the emission aperture 108 substantially aligns with the fluorescence emission discharge aperture 103. The analysis scanner 300 may move laterally in either direction horizontally along the stepper screw 402 via the stepper motor 401 rotating the stepper screw 402 clockwise or counter-clockwise. The stepper screw 402 and the stepper screw hole 111 may be threaded where the movement of the analysis scanner 300 by the stepper motor 401 is constrained by a threaded movement.

The stepper motor 401, the light sources, and the photodetectors of the analysis scanner 300 may be regulated (e.g. turned on and turned off) by a controller. The controller may be configured to move the analysis scanner 300 backward and forward along the heating block 100 in a predetermined amount via the stepper screw 402, to turn the light sources on and off, to turn the photodetectors on and off, to turn the heating element 404 of the heating block 100 on and off, and to reset the analysis scanner. For example, the controller may regulate the stepper motor, light sources, and photodetectors in a sequence or combination. A computer program may be used to configure the controller.

Figure 7:
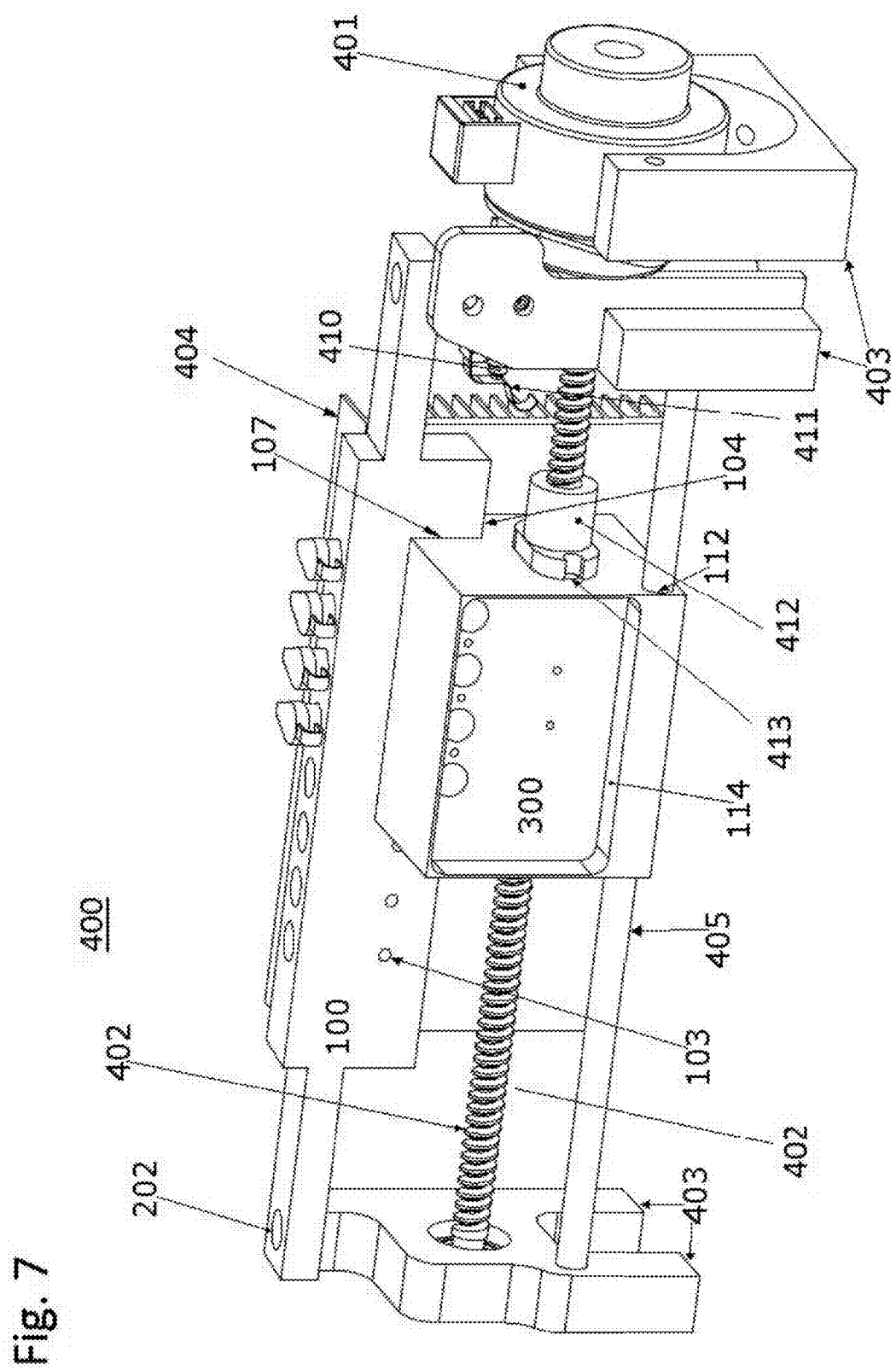
FIG. 7 represents another wavelength scanning apparatus.

FIG. 7 represents a wavelength scanning apparatus. The wavelength scanning apparatus 400 includes a heating block 100, an analysis scanner 300, a stepper motor 401, a stepper screw 402, a stepper screw hole 111, and a structural support 403 having a guide rail 405 as described in FIG. 1. The wavelength scanning apparatus 400 also includes a reset button 410, a reset trigger 411, at least one stepper nut screw 412, and a stepper nut 413. The reset button 410 is in mechanical communication with the structural support 403. The reset trigger 411 is in mechanical communication with the reset button 410 and the structural support 403. The reset button 410 and the reset trigger 411 are configured to align the analysis scanner 300 with the florescence emission discharge aperture 103 prior to and/or after fluorescence detection analysis. The reset button 410 may be in electronic communication with a controller, such that the controller may initiate a reset of the analysis scanner after each fluorescence detection analysis. The reset of the analysis scanner 300 provides that the analysis scanner 300 is in the same alignment with the florescence emission discharge aperture 103 for each fluorescence detection analysis.

The stepper nut screw 412 is in mechanical communication with the analysis scanner 300 and the stepper screw 402. The stepper nut 413 is in mechanical communication with the stepper nut screw 412 and the stepper screw 402. The stepper nut screw 412 and the stepper nut 413 are configured for securing the analysis scanner to the stepper screw 402.

FIG. 2A is a vertical cross sectional view of the heating block 100. Sample wells 101 have a shape configured to hold a sample, for example, a 0.2 ml PCR tube. The excitation activation aperture 102 may be, for example, 2 mm in diameter and cylindrical in shape. The fluorescence emission discharge aperture 103 may be, for example, cone shaped with a diameter of 2 mm at the back and 1 mm at the front.

Figure 2B:
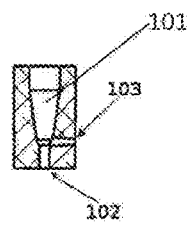
FIG. 2B is a vertical cross section view of a well of the wavelength scanning apparatus.

FIG. 2B shows a vertical cross sectional view of the sample well 101. The sample well 101 has a shape configured to hold a sample, for example, a 0.2 ml PCR tube. The excitation activation aperture 102 may be, for example, 2 mm in diameter and cylindrical in shape. The fluorescence emission discharge aperture 103 may be, for example, cone shaped with a diameter of 2 mm at the back and 1 mm at the front.

Figure 8A:
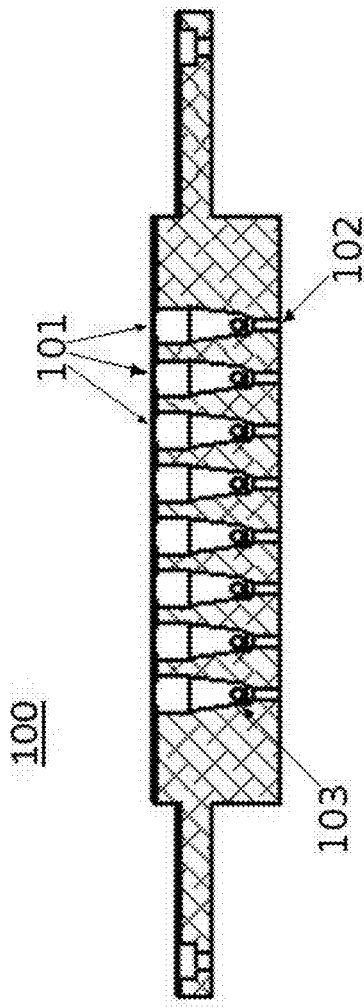
FIG. 8A is a vertical cross sectional view of a heating block of the wavelength scanning apparatus.

FIG. 8A is a vertical cross sectional view of the heating block 100. The fluorescence emission discharge aperture 103 may be cylindrical in shape with a diameter of 2 mm. The fluorescence emission discharge aperture may be from 0.5 mm to 3.0 mm from the top of the excitation activation aperture 103. The front of the heating block 100 may be lower than the back of the heating block 100, such that there is angled downward slope from the back to the front of the heating block 100. The front of the heating block 100 may be 4 mm higher than the back of the heating block 100.

Figure 8B:
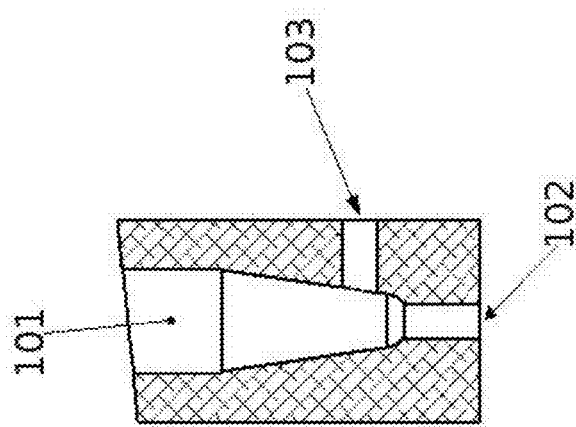
FIG. 8B is a vertical cross section view of a well of the wavelength scanning apparatus.

FIG. 8B shows a vertical cross sectional view of the sample well 101. The fluorescence emission discharge aperture 103 may be cylindrical in shape with a diameter of 2 mm. The fluorescence emission discharge aperture may be from 0.5 mm to 3.0 mm from the top of the excitation activation aperture 103.

FIGS. 3A and 3B represent a front side angled view and a back side angled view, respectively, of the analysis scanner 300 of the wavelength scanning apparatus. The analysis scanner 300 includes a flat surface 104, a front wall 107, a side surface 110, at least four excitation apertures 105, at least four emission apertures 108, at least four excitation light filters 130, at least four fluorescence emission light filters 120, an excitation recessed area 113, an emission recessed area 114, at least four light sources 150, and at least four photo detectors 140. The at least four light sources may originate from a single light source that is split by way of light channels, light pipes, and the like to provide the at least four light sources, or from multiple light sources.

The analysis scanner 300 has dimensions that correspond with dimensions of and substantial alignment of apertures with the heating block 100. Such dimension correspondence is explained further in paragraphs that follow in relation to the operation of the wavelength scanning apparatus 400.

The analysis scanner 300 has a stepping block shape, where a front of the analysis scanner 300 has a step indentation formed by the flat surface 104 being substantially perpendicular with the front wall 107 along a top side of the analysis scanner 300. For example, the flat surface 104 extends toward the back of the analysis scanner 300 until the flat surface 104 meets the front wall 107 in a perpendicular manner, such that the step indentation forms an approximate right angle. The flat surface 104 may have a depth of 10.5 mm, and the front wall 107 may have a height of 9.5 mm.

The analysis scanner 300 may have an excitation aperture 105 having a top and a bottom. The excitation aperture 105 extends from the flat surface 104 downward to the excitation recessed area 113 at the bottom of the analysis scanner 300. The excitation aperture 105 may be cylindrical with a diameter of 6.45 mm at the bottom and 4 mm at the top. The analysis scanner 300 may have an emission aperture 108 having a front and a back. The emission aperture 108 extends from the front wall 107 backward to the emission recessed area 114 at the back of the analysis scanner 300. The emission aperture 108 may be cone shaped having a diameter of 4 mm at the front and 6.45 mm at the back. The emission aperture 108 may be cylindrical having a diameter of 2.5 mm. The analysis scanner 300 may have an excitation light filter 130. The excitation light filter 130 may be set inside the excitation aperture 105 toward the flat surface 104 and configured for filtering out wavelengths of light except that of an excitation wavelength. For example, a first excitation light filter is configured to filter light except light of the absorption wavelength of a first fluorophore (e.g. 494 nm, 500 nm), a second excitation light filter is configured to filter light except light of the absorption wavelength of a second flurophore (e.g. 515 nm, 564 nm), a third excitation light filter is configured to filter light except light of the absorption wavelength of a third fluorophore (e.g. 559 nm, 645 nm), and a fourth excitation light filter is configured to filter light expect light of the absorption wavelength of a fourth fluorophore (e.g. 647 nm, 747 nm).

The analysis scanner 300 may have a fluorescence emission light filter 120. The fluorescence emission light filter 120 may be set inside the emission aperture 108 toward the front wall 107 and configured for filtering out wavelengths of light except that of a fluorescent emission wavelength. For example, a first fluorescence light filter is configured to filter light except light of the fluorescent emission wavelength of the first fluorophore (e.g. 521 nm, 520 nm), a second fluorescence light filter is configured to filter light except light of the fluorescent emission wavelength of the second fluorophore (e.g. 650 nm, 590 nm), a third fluorescence light filter is configured to filter light except light of the fluorescent emission wavelength of the third fluorophore (e.g. 578 nm, 671 nm), and a fourth fluorescence light filter is configured to filter light except light of the fluorescent emission wavelength of the fourth fluorophore (e.g. 670 nm, 776 nm).

The scanner 300 has a plurality of light sources 150 wherein a first light source is configured to emit light of a first wavelength to excite the first fluorophore corresponding to a first nucleic acid primer (e.g. DNA primer, RNA primer), a second light source is configured to emit light of a second wavelength to excite the second fluorophore corresponding to a second nucleic acid primer, a third light source is configured to emit light of a third wavelength to excite the third fluorophore corresponding to a third nucleic acid primer, and a fourth light source is configured to emit light of a fourth wavelength to excite the fourth fluorophore corresponding to a fourth nucleic acid primer. The scanner 300 contains a plurality of photodetectors 140 configured to detect fluorescent emission wavelengths from the plurality of fluorophores. For example, a first photodetector is configured to detect the fluorescent emission wavelength from the first fluorophore, a second photodetector is configured to detect the fluorescent emission wavelength from the second fluorophore, a third photodetector is configured to detect the fluorescent emission wavelength from the third fluorophore, and a fourth photodetector is configured to detect the fluorescent emission wavelength from the fourth fluorophore. The plurality of photodetectors 140 may be photodiodes that detect the photons of the fluorescent emission wavelength.

Referring to FIG. 3B the excitation recessed area 113 is a recessed area on the bottom of the analysis scanner 300. The excitation recessed area 113 may be rectangular in shape and have dimensions that correspond with the dimensions of the analysis scanner 300. For example, the excitation recessed area 113 may be 45.5 mm length, 21.14 mm height, and 6 mm depth. The excitation recessed area 113 may be sized for receiving an excitation printed circuit board. The excitation printed circuit board includes a plurality of light sources. The light sources preferably are light emitting diodes (LEDs) capable of emitting light at a plurality of different excitation wavelengths. Each light source is of slightly smaller diameter than the diameter of the excitation aperture 105 such that when the circuit board is received by the excitation recessed area 113, each light source fits within the corresponding excitation aperture 105. The excitation printed circuit board may be secured to the excitation recessed area 113 by screwing the circuit board into the analysis scanner 300 at a plurality of excitation circuit holes 302.

Referring to FIG. 3B the emission recessed area 114 is a recessed area on the back of the analysis scanner 300. The emission recessed area 114 may be rectangular in shape and has dimensions that correspond with the dimensions of the analysis scanner 300. For example, the emission recessed area 114 may be a height of 18 mm, a length of 45.5 mm, and a depth of 6 mm. The emission recessed area 114 may be configured for receiving an emission printed circuit board. The emission printed circuit board includes at least four photodetectors. Each photodetector preferably is a photodiode configured for detecting at least one fluorescent emission wavelength. The photodetector is of slightly smaller diameter than the diameter of the emission aperture 108 such that when the circuit board is received by the emission recessed area 114, each photodetector fits within the corresponding emission aperture 108. The circuit board may be secured to the emission recessed area 114 by screwing the circuit board into the analysis scanner 300 at a plurality of emission circuit holes 303.

Referring to FIG. 3A and FIG. 3B the analysis scanner 300 may have a stepper screw hole 111 and a guide rail hole 112. The stepper screw hole 111 may be an aperture extending horizontally through the analysis scanner 300 and is configured for receiving a stepper screw 402. The stepper screw hole 111 may be a variety of lengths corresponding to the length of the analysis scanner 300; for example, the screw hole 111 may be 46.5 mm in length. The stepper screw hole 111 may be threaded where the movement of the analysis scanner 300 along the stepper screw 402 is constrained by the threads of the stepper screw hole 111 and the stepper screw 402. The stepper screw hole 111 may be unthreaded when the movement of the analysis scanner 300 along the stepper screw hole 402 is constrained by at least one stepper nut screw 412 and a stepper nut 413. The guide rail hole 112 is an aperture extending horizontally through the analysis scanner 300 and is configured to receive a guide rail. The guide rail hole 112 may be a variety of lengths corresponding to the length of the analysis scanner 300; for example, the guide rail hole may be 46.5 mm in length. In embodiments, the guide rail may be connected to the structural support 403 and may be configured to hold the analysis scanner 300 in place within the wavelength scanning apparatus 400.

Figure 4:
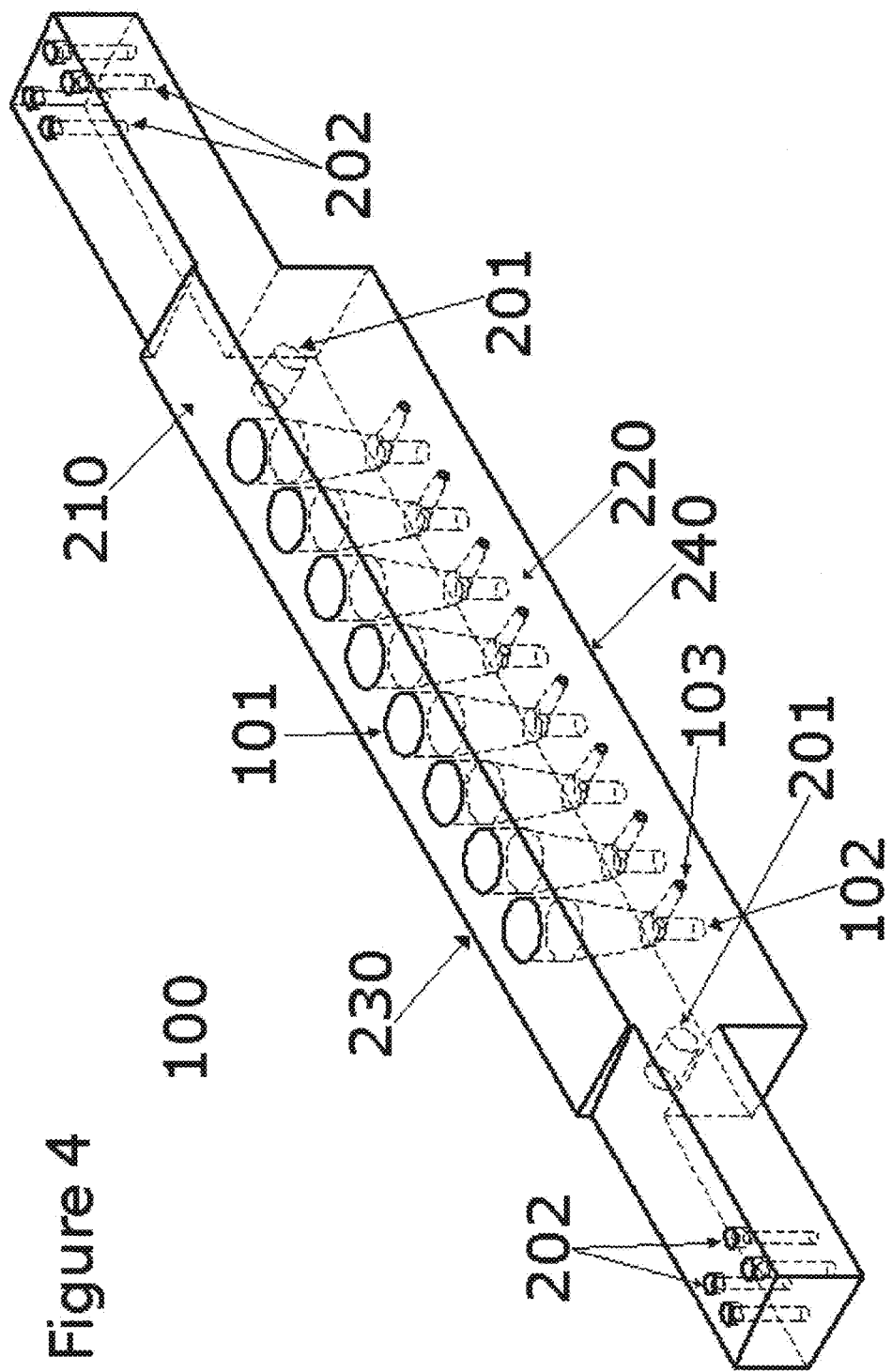
FIG. 4 depicts a heating block of a wavelength scanning apparatus.
Figure 5:
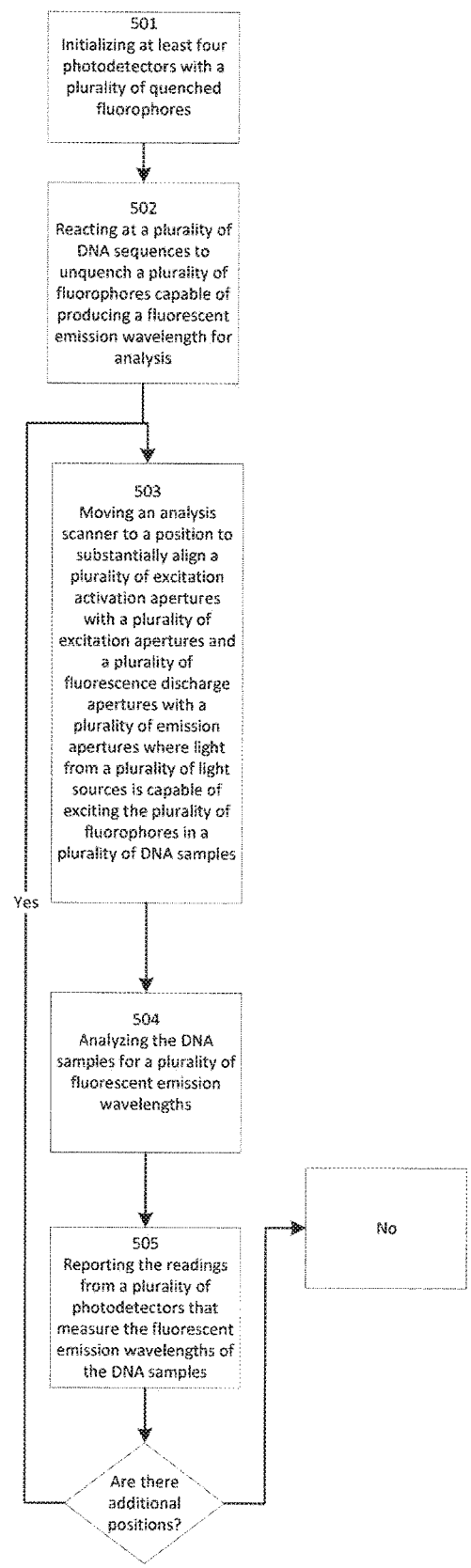
FIG. 5 illustrates a method for testing for the presence of nucleic acid samples using the wavelength scanning apparatus.

FIG. 4 depicts a heating block 100 of the wavelength scanning apparatus 400. The heating block 100 includes a top side 210, a bottom side 240, a front side 220, and a back side 230. The heating block 100 includes at least four sample wells 101, at least four excitation activation apertures 102, and at least four fluorescence emission discharge apertures 103. The heating block 100 may be of any metal, ceramic, or other heat resistant material, such as aluminum. The heating block 100 may be of any dimension, such as a t-block shape having a first length of 166 millimeters (mm) in length, a second length of 100 mm, a width of 12 mm, a first height of 20 mm, and a second height of 8.41 to 9.63 mm. The front 220 of the heating block 100 may be lower than the back 230 of the heating block 100, such that there is angled downward slope from the back to the front of the heating block 100. The front of the heating block 100 may be 4 mm higher than the back of the heating block 100. The sample well 101 may be formed as part of the heating block 100, where the sample well 101 is a hollowed out portion of the heating block 100, having a bottom and a top. The sample well 101 may extend from the top side 210 of the heating block 100 toward the bottom side 240 of the heating block 100 where the sample well 101 terminates in the excitation activation aperture 102. The sample well 101 may be of any shape and diameter compatible with sample retention, entry of the excitation wavelength, and exit of the fluorescent emission wavelength (e.g. cylindrical, rectangular prism, and the like). The sample well 101 may be of tapered cylindrical shape configured for fitting a 0.2 milliliter (ml) PCR tube. The excitation activation aperture 102 may extend from the bottom side of the heating block 100 toward the top side of the heating block 100 where the excitation activation aperture 102 transitions into the bottom of the sample well 101, thus forming an outlet the diameter of the excitation activation aperture 102. The excitation activation aperture 102 may substantially align with the bottom of the sample well 101 such that the approximate geometric center of the excitation activation aperture 102 substantially aligns with the geometric center of the sample well 101. The excitation activation aperture 102 may have a cylindrical shape. The excitation activation aperture 102 may have a 2 millimeter (mm) diameter.

A fluorescence emission discharge aperture 103, having a front and a back, may be formed on the front side 220 of the heating block 100 and extend toward the back side 230 of the heating block 100 where the fluorescence emission discharge aperture 103 transitions into a side of the sample well 101, forming an outlet having a diameter substantially equal to the back of the fluorescence emission discharge aperture 103, such that the excitation activation aperture 102 and the fluorescence emission discharge aperture 103 are in light communication via the sample well 101. The fluorescence emission discharge aperture 103 may be perpendicular to the sample well 101, such that an approximate right angle is formed between the excitation activation aperture 102 and the fluorescence emission discharge aperture 103. The fluorescence emission discharge aperture 103 may have a cone shape where the diameter of the front of the fluorescence emission discharge aperture 103 is smaller than the diameter of the back of the fluorescence emission discharge aperture 103. The front of the fluorescence emission discharge aperture 103 may be 1 mm in diameter and the back of the fluorescence emission discharge aperture 103 may be 2 mm in diameter. The plurality of sample wells, excitation activation apertures and discharge apertures may be substantially the same as the sample well 101, the excitation activation aperture 102, and the fluorescence emission discharge aperture 103. Other sample well designs for the heating block 100 that are compatible with the operating principles of the wavelength scanning apparatus 400 may be used.

Referring to FIG. 4, the heating block 100 may have one or more heat sink screw holes 201 and one or more heating block screw holes 202. The heat sink screw hole 201 may be configured for mounting a heating element 404, having a front side and a back side, and a heat sink, having a front side and a back side, to the heating block 100 where the front side of the heating element 404 contacts the back of the heating block 100, and the front side of the heat sink contacts the back side of the heating element 404. The heating element 404 may be a Peltier heater, and the heat sink may be a pinned heat sink. The heating block screw holes 202 may be configured for attaching the heating block 100 to the structural support 403. The structural support 403 may be configured for supporting the heating block 100 such that the wavelength scanning apparatus 400 may have its top side facing upright (or upward).

Figure 9:
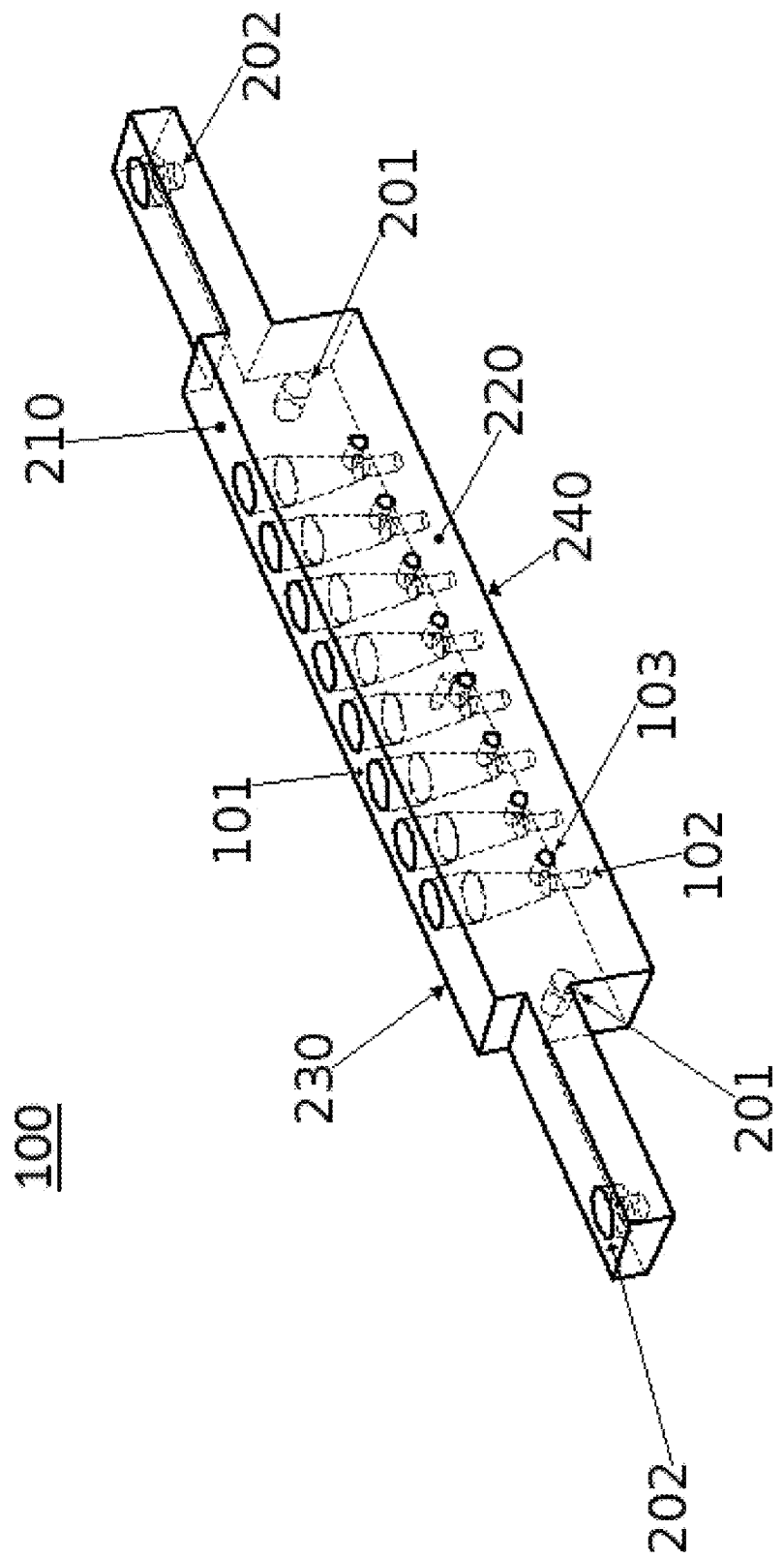
FIG. 9 is a heating block of a wavelength scanning apparatus.
Figure 10:
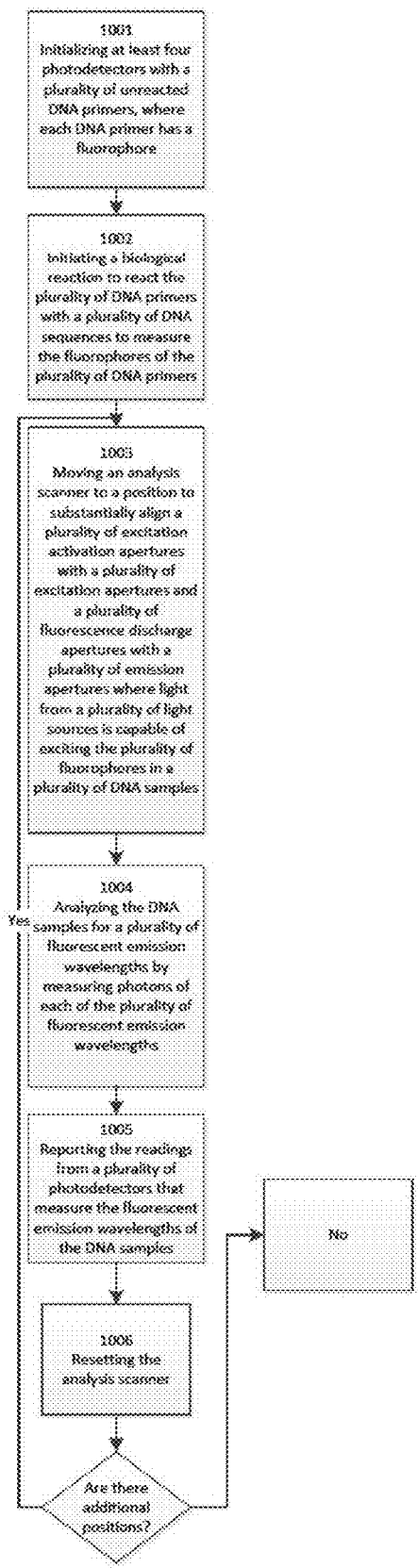
FIG. 10 illustrates a method for testing for the presence of nucleic acid samples using the wavelength scanning apparatus with a reset button.

FIG. 9 illustrates a heating block 100 of the wavelength scanning apparatus. The heating block 100 includes a top side 210, a bottom side 240, a front side 220, a back side 230, at least four sample wells 101, and at least four excitation activation apertures 102 as described in FIG. 4. The heating block 100 may include a fluorescence emission discharge aperture 103 that may be cylindrical in shape with a diameter of 2.5 mm. The fluorescence emission discharge aperture may be from 0.5 mm to 3.0 mm from the top of the florescence emission excitation activation aperture 103.

Unlike in FIG. 1, FIG. 2A, and FIG. 4, where the wavelength scanning apparatus 400 is represented with eight of the sample wells 101 in the heating block 100, when the heating block 100 includes four of the sample wells 101 and the analysis scanner 300 includes four sets of apertures, the analysis scanner 300 may move to a series of positions as represented in FIG. 6. Referring to FIG. 6, in a first position 610 a first excitation activation aperture is substantially aligned with a fourth excitation aperture and a first fluorescence emission discharge aperture is substantially aligned with a fourth emission aperture. The movement of the analysis scanner 300 occurs via the stepper motor 401 wherein the stepper motor 401 is configured to turn the stepper screw 402 a predetermined distance to achieve substantial alignment of the first position.

The analysis scanner 300 then may move to a second position 620 where the first excitation activation aperture is substantially aligned with a third excitation aperture, the first fluorescence emission discharge aperture is substantially aligned with a third emission aperture, a second excitation activation aperture is substantially aligned with the fourth excitation aperture, and a second fluorescence emission discharge aperture is substantially aligned with the fourth emission aperture. The movement of the analysis scanner 300 occurs via the stepper motor 401 where the stepper motor 401 is configured to turn the stepper screw 402 a predetermined distance to achieve substantial alignment of the second position.

The analysis scanner 300 then may move to a third position 630 where the first excitation activation aperture is substantially aligned with a second excitation aperture, the first fluorescence emission discharge aperture is substantially aligned with a second emission aperture, the second excitation activation aperture is substantially aligned with the third excitation aperture, the second fluorescence emission discharge aperture is substantially aligned with the third emission aperture, a third excitation activation aperture is substantially aligned with the fourth excitation aperture, and a third fluorescence emission discharge aperture is substantially aligned with the fourth emission aperture. The movement of the analysis scanner 300 occurs via the stepper motor 401 where the stepper motor 401 is configured to turn the stepper screw 402 a predetermined distance to achieve substantial alignment of the third position.

The analysis scanner 300 then may move to a fourth position 640 where the first excitation activation aperture is substantially aligned with a first excitation aperture, the first fluorescence emission discharge aperture is substantially aligned with a first emission aperture, the second excitation activation aperture is substantially aligned with the second excitation aperture, the second fluorescence emission discharge aperture is substantially aligned with the second emission aperture, the third excitation activation aperture is substantially aligned with the third excitation aperture, the third fluorescence emission discharge aperture is substantially aligned with the third emission aperture, a fourth excitation activation aperture is substantially aligned with the fourth excitation aperture, and a fourth fluorescence emission discharge aperture is substantially aligned with the fourth emission aperture. The movement of the analysis scanner 300 occurs via the stepper motor 401 where the stepper motor 401 is configured to turn the stepper screw 402 a predetermined distance to achieve substantial alignment of the fourth position. In the fourth position, the analysis scanner 300 detects four fluorescent emission wavelengths simultaneously or nearly simultaneously.

The analysis scanner 300 then may move to a fifth position 650 where the second excitation activation aperture is substantially aligned with the first excitation aperture, the second fluorescence emission discharge aperture is substantially aligned with the first emission aperture, the third excitation activation aperture is substantially aligned with the second excitation aperture, the third fluorescence emission discharge aperture is substantially aligned with the second emission aperture, the fourth excitation activation aperture is substantially aligned with the third excitation aperture, and the fourth fluorescence emission discharge aperture is substantially aligned with the third emission aperture. The movement of the analysis scanner 300 occurs via the stepper motor 401 where the stepper motor 401 is configured to turn the stepper screw 402 a predetermined distance to achieve substantial alignment of the fifth position.

The analysis scanner 300 then may be moved to a sixth position 660 where the third excitation activation aperture is substantially aligned with the first excitation aperture, the third fluorescence emission discharge aperture is substantially aligned with the first emission aperture, the fourth excitation activation aperture is substantially aligned with the second excitation aperture, and the second fluorescence emission discharge aperture is substantially aligned with the fourth emission aperture. The movement of the analysis scanner 300 occurs via the stepper motor 401 where the stepper motor 401 is configured to turn the stepper screw 402 a predetermined distance to achieve substantial alignment of the sixth position.

The analysis scanner 300 then may be moved to a seventh position 670 where the fourth excitation activation aperture is substantially aligned with the first excitation apertures and the fourth fluorescence emission discharge aperture is substantially aligned with the first emission aperture. The movement of the analysis scanner 300 occurs via the stepper motor 401 where the stepper motor 401 is configured to turn the stepper screw 402 a predetermined distance to achieve substantial alignment of the seventh position. Upon completion of detection in positions one through seven, detection of four different fluorescent emission wavelengths has occurred from each of the four different sample wells 101 with different fluorescent emission wavelengths.

A method 500 is used to analyze at least four deoxyribonucleic acid (DNA) samples for at least four different DNA sequences (e.g. nucleotides or oligonucleotides). A DNA sample may contain all, some, or none of the DNA sequences. Each DNA sample includes a plurality of DNA primers to detect the DNA sequences that are present in each sample. Each DNA primer could be labeled with a fluorophore, each fluorophore having unique absorption and emission properties. Detection of the DNA sequences by fluorescence emission via fluorophores may occur through primer extension of a probe as a result of using labeled nucleotides, through molecular beacon or similar fluorophore, and through quencher based primers or other means to detect fluorescence. For example, a first DNA primer may be labeled with a fluorophore that absorbs light at a wavelength of 494 nanometers (nm) and fluoresces at a wavelength of 521 nm (e.g. DY495), a second DNA primer may be labeled with a fluorophore that absorbs light at a wavelength of 515 nm and fluoresces at a wavelength of 650 nm (e.g. DY481-XL), a third DNA primer may be labeled with a fluorophore that absorbs light at a wavelength of 559 nm and fluoresces at a wavelength of 578 nm (e.g. DY560), and a fourth DNA primer may be labeled with a fluorophore that absorbs light at a wavelength of 647 nm and fluoresces at a wavelength of 670 nm (e.g. DY636). Each of the first, second, third, and fourth DNA primers reside in each of the at least four PCR tubes of a 0.2 ml volume having a plurality of DNA samples. For example, a first PCR tube contains a first DNA sample and the first, second, third, and fourth DNA primers, a second PCR tube contains a second DNA sample and the first, second, third, and fourth DNA primers, a third PCR tube contains the third DNA sample and the first, second, third, and fourth DNA primers, and a fourth PCR tube contains a fourth DNA sample and the first, second, third, and fourth DNA primers.

In 501, the wavelength scanning apparatus 400 is initialized to determine background fluorescence for each of the at least four different DNA samples, where each of the at least four different DNA samples includes at least one fluorophore. Each of the different DNA samples may contain from one to four fluorophores for detection. Each of the different DNA samples also may contain at least four fluorophores. Thus, during 501 the wavelength scanning apparatus 400 determines the amount and/or wavelength of fluorescence emission produced from each DNA sample that is not in response to a desired analyte. For example, in molecular beacon fluorescence, before initiation of the PCR reaction which binds a primer to a DNA sequence of interest, the fluorophore is bound by a quencher and therefore will not produce a recordable fluorescent emission wavelength indicative of the presence of the DNA sequence of interest. Initialization may occur for each DNA sample wherein a light source is turned on for a period of time (e.g. 5 seconds) to emit light of a first wavelength that travels through an excitation activation aperture, an excitation aperture, an excitation light filter, the DNA sample, a fluorescence emission discharge aperture, an emission aperture, and a fluorescence emission light filter until it reaches a photodetector configured for detecting light of a second wavelength that corresponds to the first wavelength. Initialization of each DNA sample occurs when a DNA sample is in the sample well 101 where the excitation activation aperture 102 is substantially aligned with the excitation aperture 105 and the fluorescence emission discharge aperture 103 is substantially aligned with the emission aperture 108 of the analysis scanner 300. For example, in the fourth position the first, second, third, and fourth DNA samples are initialized simultaneously or nearly simultaneously. The initial reading of the wavelength by the photodetector for a DNA primer in a DNA sample is read by and stored in a computer program to determine the amount of background fluorescence of the wavelength in a DNA sample.

In 502, the biological reaction is initiated. The biological reaction may be the amplification of DNA using polymerase chain retain (PCR) or any other isothermal amplification method compatible with the sample and the analysis. Initiation 502 may include raising and lowering the temperature of the heating block 100 to predetermined temperatures where the DNA primers will anneal to the corresponding DNA sequence and amplify by PCR or other amplification method. Annealing of the DNA primers to the corresponding DNA sequences unquenches the fluorophore by separation of the fluorophore and quencher such that the fluorophore may produce a recordable fluorescent emission wavelength.

In 503, the analysis scanner 300 is moved a position. At each position 1 through 7 for a wavelength scanning apparatus 400 with four of the sample wells 101, the excitation activation aperture 102 is substantially aligned with the excitation aperture 105 and the fluorescence emission discharge aperture 103 is substantially aligned with the emission aperture 108 of the analysis scanner 300. For example, in the fourth position, each of the four excitation activation apertures are substantially aligned with each of the four excitation apertures and each of the four fluorescence emission discharge apertures are substantially aligned with each of the four emission apertures.

In 504, each DNA sample is analyzed for the presence and optionally the quantity of a plurality of DNA sequences by detection of the desired fluorescent emission wavelengths. Analysis may occur at positions 1 through 7 wherein a plurality of light sources are turned on for a period of time (e.g. 5 seconds) to emit light of a first excitation wavelength that travels through an excitation activation aperture, an excitation aperture, an excitation light filter, and a DNA sample to excite a fluorophore. The resulting fluorescent emission wavelength then travels to a fluorescence emission discharge aperture, an emission aperture, and a fluorescence emission light filter until it reaches a photodetector configured for detecting light of a second emission wavelength. For example, in the fourth position detection of the first, second, third, and fourth DNA samples are tested simultaneously or nearly simultaneously, each at a different excitation wavelength. The detection reading of the wavelength by the photodetector is read by and stored by a computer program to determine the presence, absence, and/or quantity of a DNA sequence in a DNA sample.

In 505, the wavelength scanning apparatus 400 reports the presence, absence, and/or quantity of the selected DNA sequence/s in each DNA sample. This information may be displayed, stored, transmitted, or otherwise processed. Steps 503, 504, and 505 may be repeated at each position 1 through position 7.

It is to be noted that the foregoing described embodiments may be conveniently implemented using conventional general purpose digital computers programmed according to the teachings of the present specification, as will be apparent to those skilled in the computer art. Appropriate software coding may readily be prepared by skilled programmers based on the teachings of the present disclosure, as will be apparent to those skilled in the software art.

It is to be understood that the embodiments described herein may be conveniently implemented in forms of a software package. Such a software package may be a computer program product which employs a non-transitory computer-readable storage medium including stored computer code which is used to program a computer to perform the disclosed functions and processes disclosed herein. The non-transitory computer-readable storage medium may include, but is not limited to, any type of conventional floppy disk, optical disk, CD-ROM, magnetic disk, hard disk drive, magneto-optical disk, ROM, RAM, EPROM, EEPROM, magnetic or optical card, or any other suitable non-transitory media for storing electronic instructions.

A method 1000 is used to analyze at least four nucleic acid (e.g. DNA or ribonucleic acid (RNA)) samples for at least four different nucleic acid sequences (e.g. nucleotides or oligonucleotides). A nucleic acid sample may contain all, some, or none of the nucleic acid sequences. Each nucleic acid sample includes a plurality of nucleic acid primers to detect the nucleic acid sequences that are present in each sample. Each nucleic acid primer could be labeled with a fluorophore, each fluorophore having unique absorption and emission properties. Detection of the nucleic acid sequences by fluorescence emission via fluorophores may occur through primer extension of a probe as a result of using labeled nucleotides, through molecular beacon or similar fluorophore, and through quencher based primers or other means to detect fluorescence.

For example, a first nucleic acid primer may be labeled with a fluorophore that absorbs light at a wavelength of 500 nanometers (nm) and fluoresces at a wavelength of 520 nm (e.g. Atto 488), a second nucleic acid primer may be labeled with a fluorophore that absorbs light at a wavelength of 564 nm and fluoresces at a wavelength of 590 nm (e.g. Atto 565), a third nucleic acid primer may be labeled with a fluorophore that absorbs light at a wavelength of 645 nm and fluoresces at a wavelength of 671 nm (e.g. DY636), and a fourth nucleic acid primer may be labeled with a fluorophore that absorbs light at a wavelength of 747 nm and fluoresces at a wavelength of 776 nm (e.g. DY750). Each of the first, second, third, and fourth nucleic acid primers reside in each of the at least four PCR tubes of a 0.2 ml volume having a plurality of nucleic acid samples. For example, a first PCR tube contains a first nucleic acid sample and the first, second, third, and fourth nucleic acid primers, a second PCR tube contains a second nucleic acid sample and the first, second, third, and fourth nucleic acid primers, a third PCR tube contains the third nucleic acid sample and the first, second, third, and fourth nucleic acid primers, and a fourth PCR tube contains a fourth nucleic acid sample and the first, second, third, and fourth nucleic acid primers.

In 1001, the wavelength scanning apparatus 400 is initialized to determine background fluorescence for each of the at least four different nucleic acid samples, where each of the at least four different nucleic acid samples includes at least one fluorophore. Each of the different nucleic acid samples may contain from one to four fluorophores for detection. Each of the different nucleic samples also may contain at least four fluorophores. Thus, during 1001 the wavelength scanning apparatus 400 determines the amount (e.g. intensity) of the wavelength of fluorescence emission produced from each nucleic acid sample that is not in response to a desired analyte. For example, in molecular beacon fluorescence, before initiation of the PCR reaction which binds a primer to a nucleic acid sequence of interest, the fluorophore is bound by a quencher and therefore will not produce a recordable fluorescent emission wavelength indicative of the presence of the nucleic acid sequence of interest. Initialization may occur for each nucleic acid sample wherein a light source is turned on for a period of time (e.g. from 0.5 to 5 seconds) to emit light of a first wavelength that travels through an excitation activation aperture, an excitation aperture, an excitation light filter, the nucleic acid sample, a fluorescence emission discharge aperture, an emission aperture, and a fluorescence emission light filter until it reaches a photodetector configured for detecting light (e.g. photons) of a second wavelength that corresponds to the first wavelength. Initialization of each nucleic acid sample occurs when a nucleic acid sample is in the sample well 101 where the excitation activation aperture 102 is substantially aligned with the excitation aperture 105 and the fluorescence emission discharge aperture 103 is substantially aligned with the emission aperture 108 of the analysis scanner 300. For example, in the fourth position the first, second, third, and fourth nucleic acid samples are initialized simultaneously or nearly simultaneously. The initial reading of the wavelength by the photodetector for a nucleic acid primer in a nucleic acid sample is read by and stored in a computer program to determine the amount of background fluorescence of the wavelength in a nucleic acid sample.

In 1002, the biological reaction is initiated. The biological reaction may be the amplification of nucleic acid using polymerase chain retain (PCR), reverse transcription PCR, or any other isothermal amplification method compatible with the sample and the analysis. Initiation 1002 may include raising and lowering the temperature of the heating block 100 to predetermined temperatures where the nucleic acid primers will anneal to the corresponding nucleic acid sequence and amplify by PCR or other amplification method. Annealing of the nucleic acid primers to the corresponding nucleic acid sequences unquenches the fluorophore by separation of the fluorophore and quencher such that the fluorophore may produce a recordable fluorescent emission wavelength.

In 1003, the analysis scanner 300 is moved to a position. At each position 1 through 7 for a wavelength scanning apparatus 400 with four of the sample wells 101, the excitation activation aperture 102 is substantially aligned with the excitation aperture 105 and the fluorescence emission discharge aperture 103 is substantially aligned with the emission aperture 108 of the analysis scanner 300. For example, in the fourth position, each of the four excitation activation apertures are substantially aligned with each of the four excitation apertures and each of the four fluorescence emission discharge apertures are substantially aligned with each of the four emission apertures. The analysis scanner 300 may be moved to the position by a controller.

In 1004, each nucleic acid sample is analyzed for the presence and optionally the quantity of a plurality of nucleic acid sequences by detection of the desired fluorescent emission wavelengths. Analysis may occur at positions 1 through 7 wherein a plurality of light sources are turned on for a period of time (e.g. from 0.5 to 5 seconds) to emit light of a first excitation wavelength that travels through an excitation activation aperture, an excitation aperture, an excitation light filter, and a nucleic acid sample to excite a fluorophore. The resulting fluorescent emission wavelength then travels to a fluorescence emission discharge aperture, an emission aperture, and a fluorescence emission light filter until it reaches a photodetector configured for detecting light (e.g. photons) of a second emission wavelength. For example, in the fourth position detection of the first, second, third, and fourth nucleic acid samples are tested simultaneously or nearly simultaneously, each at a different excitation wavelength. The detection reading of the wavelength by the photodetector is read by and stored by a computer program to determine the presence, absence, and/or quantity of a nucleic acid sequence in a nucleic acid sample.

In 1005, the wavelength scanning apparatus 400 reports the presence, absence, and/or quantity of the selected nucleic acid sequence/s in each nucleic acid sample. This information may be displayed, stored, transmitted, or otherwise processed. Steps 503, 504, and 505 may be repeated at each position 1 through position 7.

In 1006, the wavelength scanning apparatus resets to align the analysis scanner. The reset includes the analysis scanner moving to a reset position where the analysis scanner contacts the reset trigger. The reset trigger activates the reset button to align the analysis scanner with the fluorescence emission discharge aperture, which ensures the same alignment for each fluorescence detection analysis. The controller may be configured to cause the analysis scanner to move to the reset position.

As used herein, the term "simultaneously or nearly simultaneously" means that while detection of multiple wavelength fluorescence at a particular position (e.g. position 4) has occurred simultaneously, particular fluorophores have distinct quantum efficiencies, such that fluorescence occurs at a different time (e.g. milliseconds) as compared to another particular fluorophore.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It is believed that the present invention and many of its attendant advantages will be understood from the foregoing description. It is also believed that it will be apparent that various changes may be made in the form, construction and arrangement of the components thereof without departing from the scope and spirit of the invention or without sacrificing all of its material advantages. The form hereinbefore described being merely an explanatory embodiment thereof, it is the intention of the following claims to encompass and include such changes.

The invention claimed is:

1. A wavelength scanning apparatus for measuring fluorescence emission of a plurality of nucleic acid samples, comprising:
   a structural support, the structural support
      comprising a reset button and a reset
      trigger, wherein
         the reset button is in mechanical communication with the reset trigger; a heating block attached to the structural support, the heating block comprising
         a plurality of sample wells, wherein
            each of the plurality of sample wells forms an opening on a top side of the
         heating block,
         a plurality of excitation activation apertures, and
         a plurality of fluorescence discharge apertures, wherein
         each of the plurality of sample wells transitions to a corresponding excitation activation aperture of the plurality of excitation activation apertures and a corresponding fluorescence discharge aperture of the plurality of excitation activation apertures, and wherein
         each of the plurality of excitation activation apertures forms an opening on a bottom side of the heating block and each of the plurality of fluorescence discharge apertures forms an opening on a front side of the heating block;
      a stepper motor attached to the structural support;
   an analysis scanner attached to the stepper motor, where the stepper motor moves the analysis scanner laterally, wherein the analysis scanner comprises
      a flat surface, the flat surface comprising a plurality of excitation apertures, where each of the plurality of excitation apertures comprises a top and a bottom, and where
         each of the plurality of excitation apertures comprises an excitation light filter; a front wall, the front wall having a plurality of emission apertures, where each of the plurality of emission apertures comprises a back and a front, and where
         each of the plurality of emission apertures comprises a fluorescence emission light filter;
      a plurality of light sources, where
         each of the plurality of light sources is disposed in a corresponding excitation aperture of the plurality of excitation apertures;
      a plurality of photodetectors, where
         each of the plurality of photodetectors is disposed in a corresponding emission aperture of the plurality of emission apertures;
   and where the flat surface of the analysis scanner substantially aligns with the bottom side of the heating block and the front wall of the analysis scanner substantially aligns with the front side of the heating block.

2. The wavelength scanning apparatus of claim 1, wherein the fluorescence emission discharge aperture of the heating block is from 0.5 to 3.0 millimeters from the top of the excitation activation aperture.

3. The wavelength scanning apparatus of claim 2, wherein the fluorescence emission discharge aperture of the heating block is cylindrical having a diameter of 2 millimeters.

4. A nucleic acid analysis method for performing fluorescence detection of multiple fluorescence emission wavelengths simultaneously or nearly simultaneously, comprising:
   initializing a first photodetector and a second photodetector with at least a first quenched fluorophore and a second quenched fluorophore;
   reacting a first nucleic acid sequence to unquench the first fluorophore to provide a first unquenched fluorophore, and a second nucleic acid sequence to unquench the second fluorophore to provide a second unquenched fluorophore, wherein
      a first nucleic acid sample contains the first nucleic acid sequence and the second nucleic acid sequence, and a second nucleic acid sample contains the first nucleic acid sequence and the second nucleic acid sequence;
   moving an analysis scanner to a position to substantially align a first excitation activation aperture with a first excitation aperture and a first fluorescence discharge aperture with a first emission aperture where a first light source is capable of exciting the first unquenched fluorophore in the first nucleic acid sample, and a second excitation activation aperture with a second excitation aperture and a second fluorescence discharge aperture with a second emission aperture where a second light source is capable of exciting the second unquenched fluorophore in the second nucleic acid sample;
   analyzing a first fluorescent emission wavelength by a first photodetector for a first fluorescent emission wavelength, and analyzing a second fluorescent emission wavelength by a second photodetector for a second fluorescent emission wavelength; and
   reporting the readings from the first photodetector and the second photodetector to detect the first fluorescent emission wavelength and the second fluorescent emission wavelengths nearly simultaneously.

5. The method of claim 4, further comprising
   initializing a third photodetector with a third quenched fluorophore;
   reacting a third nucleic acid sequence to unquench the third fluorophore to provide a third unquenched fluorophore, wherein
   the first nucleic acid sample further contains the third nucleic acid sequence, the second nucleic acid sample further contains the third nucleic acid sequence, and a third nucleic acid sample contains the first nucleic acid sequence, the second nucleic acid sequence, and the third nucleic acid sequence;
   moving the analysis scanner to a position to substantially align a third excitation activation aperture with a third excitation aperture and a third fluorescence discharge aperture with a third emission aperture where a third light source is capable of exciting the third unquenched fluorophore in the third nucleic acid sample;

analyzing a third fluorescent emission wavelength by a third photodetector for a third fluorescent emission wavelength; and reporting the readings from the first photodetector, the second photodetector, and the third photodetector to detect the first fluorescent emission wavelength, the second fluorescent emission wavelength, and the third fluorescent emission wavelength nearly simultaneously.

6. The method of claim 5, further comprising initializing a fourth photodetector with a fourth quenched fluorophore;

reacting a fourth nucleic acid sequence to unquench the fourth fluorophore to provide a fourth unquenched fluorophore, wherein the first nucleic acid sample further contains the fourth nucleic acid sequence, the second nucleic acid sample further contains the fourth nucleic acid sequence, the third nucleic acid sample further contains the fourth nucleic acid sequence, and a fourth nucleic acid sample contains the first nucleic acid sequence, the second nucleic acid sequence, the third nucleic acid sequence, and the fourth nucleic acid sequence;

moving the analysis scanner to a position to substantially align a fourth excitation activation aperture with a fourth excitation aperture and a fourth fluorescence discharge aperture with a fourth emission aperture where a fourth light source is capable of exciting the fourth unquenched fluorophore in the fourth nucleic acid sample;

analyzing a fourth fluorescent emission wavelength by a fourth photodetector for a fourth fluorescent emission wavelength; and reporting the readings from the first photodetector, the second photodetector, the third photodetector, and the fourth photodetector to detect the first fluorescent emission wavelength, the second fluorescent emission wavelength, the third fluorescent emission wavelength, and the fourth fluorescent emission wavelength nearly simultaneously.

7. The method of claim 6, further comprising repeating the moving, the analyzing, and the reporting when the first, second, third, and fourth nucleic acid samples contain unanalyzed fluorophores.

* * * * *